US008628678B2

(12) United States Patent
Voipio

(10) Patent No.: US 8,628,678 B2
(45) Date of Patent: Jan. 14, 2014

(54) METHOD FOR MEASURING THE ACTIVE KOH CONCENTRATION IN A KOH ETCHING PROCESS

(75) Inventor: Ville Voipio, Helsinki (FI)

(73) Assignee: Janesko Oy, Vantaa (FI)

( * ) Notice: Subject to any disclaimer, the term of this patent is extended or adjusted under 35 U.S.C. 154(b) by 701 days.

(21) Appl. No.: 12/443,265

(22) PCT Filed: Oct. 11, 2006

(86) PCT No.: PCT/FI2006/050436
§ 371 (c)(1),
(2), (4) Date: Mar. 27, 2009

(87) PCT Pub. No.: WO2008/043876
PCT Pub. Date: Apr. 17, 2008

(65) Prior Publication Data
US 2010/0025374 A1    Feb. 4, 2010

(51) Int. Cl.
*C03C 15/00* (2006.01)
*C03C 25/68* (2006.01)
*G01N 21/41* (2006.01)

(52) U.S. Cl.
USPC .............. 216/85; 216/84; 216/93; 356/128

(58) Field of Classification Search
USPC ............................................................ 216/85
See application file for complete search history.

(56) References Cited

U.S. PATENT DOCUMENTS

| 6,609,952 | B1 * | 8/2003 | Simon .............. 451/6 |
| 2002/0018200 | A1 | 2/2002 | Salo |
| 2004/0166584 | A1 * | 8/2004 | Misra et al. .............. 436/164 |

OTHER PUBLICATIONS

K-Patents, Process Refractometer PR-03-M Brochure, Available online May 7, 2005. http://replay.web.archive.org/20050507121949/http://www.kpatents.com/1products/PR-03-M.htm.*
Seidel et al. "Anisotropic Etching of Crystalline Silicon in Alkaline Solutions." J. Electrochem. Soc. vol. 137, No. 11, p. 3612-3626.*
K-Patents, Process Refractometer PR-23-W/PR-23-M Brochure, Available online Mar. 11, 2006. http://replay.web.archive.org/20060311134727/http://www.kpatents.com/1Library/brochures/PR-23-MandW_brochure.pdf.*
International Search Report for PCT/FI2006/050436, mailed Jun. 29, 2007.
Written Opinion of the International Searching Authority for PCT/FI2006/050436, mailed Jun. 29, 2007.
John G. Groetsch, Jr. et al., "Use of Refractive Index Analyzers for Improved Process Control," Technical Papers of ISA, Solutions for Improving Productivity and Flexibility, Technology Update LIV, International Conference and Exposition for Advancing Measurement, Control and Automation Technologies, Products and Services, ISA TECH 1999, pp. 35-43, vol. 393, Philadelphia, PA.

(Continued)

*Primary Examiner* — Allan Olsen
*Assistant Examiner* — Margaret D Klunk
(74) *Attorney, Agent, or Firm* — Buchanan Ingersoll & Rooney PC

(57) ABSTRACT

The invention relates to a method for in-line measuring the active KOH concentration in a KOH etching process in which process silicon hydroxide is produced by a reduction reaction according to the formula: $2K^+ (aq.) + 2OH^- (aq.) + 2H_2O + Si \rightarrow 2K^+ (aq.) + H_2SiO_4^{2-} (aq.) + 2H_2 (g)$. The total concentration of KOH bath is measured by using a refractometer and the measurement result is corrected by the estimated $K_2H_2SiO_4$ concentration.

2 Claims, 2 Drawing Sheets

(56) References Cited

OTHER PUBLICATIONS

Product Details of Inline Process Refractometer, from Semiconductor International [online—http://www.reed-electronics.com/semiconductor/SIproducts/CA6375428.html?text=pr%2D23%2Dm), Reed Electronics Group, Reed Business Information, Oct. 1, 2006.

European Supplemental Search Report mailed on Sep. 11, 2012, in corresponding European Application 06807993.8.

Report on KOH Process Module, retrieved from http:////www.nnf.ncsu.edu/sites/default/files/KOHReport_FINAL.pdf on Aug. 31, 2012, dated Jan. 25, 2005.

H. Seidel et al., *Anisotropic Etching of Crystalline Silicon in Alkaline Solutions*, 137(11) J. Electrochem. Soc. 3612-3626 (Nov. 1990).

K. Williams et al., *Etch Rates for Micromachining Processing*, 5(4) Journal of Microelectromechanical Systems 256-269 (Dec. 1996).

* cited by examiner

METHOD FOR MEASURING THE ACTIVE KOH CONCENTRATION IN A KOH ETCHING PROCESS

CROSS REFERENCE TO RELATED APPLICATIONS

This application is the nation stage of PCT/FI2006/050436, filed Oct. 11, 2006.

BACKGROUND

1. Field of the Invention

The invention relates to a method for in-line measuring the active KOH concentration in a KOH etching process in which process silicon hydroxide is produced by a reduction reaction according to the formula:

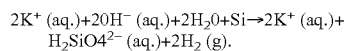
$$2K^+ (aq.) + 2OH^- (aq.) + 2H_2O + Si \rightarrow 2K^+ (aq.) + H_2SiO_4^{2-} (aq.) + 2H_2 (g).$$

2. Related Art

The actual etching reactions in KOH etching are non-trivial complicated. The reaction produces silicon hydroxide in the etching process by a reduction reaction. Silicon hydroxide, however, is not a stable compound, and it is transformed into a silicon complex. One molecule of hydrogen per one atom of silicon etched is released in the process.

The hydrogen silicate ions $H_2SiO_4^{2-}$ in the solution tend to polymerize, which sometimes leads to a 'slimy' appearance of the reaction products, and makes determining the actual reactions even more difficult.

For the sake of simplicity the reaction shown above is used here to describe the .process and the weight/weight concentration values shown later in the text paper are calculated by using the molar masses of potassium hydroxide (KOH, 56.11 g) and dipotassium hydrogen silicate ($K_2H_2SiO_4$, 172.30 g).

The etch rate of silicon in a KOH bath depends on the bath temperature and the KOH concentration. Both parameters have to be measured in order to obtain a sufficiently accurate estimate of the etching time.

SUMMARY

While measuring temperature is a trivial task, there are some challenges in the concentration measurement. As the etching progresses, KOH (and more importantly, $OH^-$ ions) is consumed, as shown in the reaction equation shown above. The byproducts (silicon complexes) do not participate in the process, but as the concentrations change, the etch rate changes.

There are measurements, e.g. refractive index measurement, capable of measuring the initial concentration of KOH in water with sufficient accuracy. However, the reaction products introduce an error into the measurement, and thus with a single measurement it is not possible to determine the actual concentration of $OH^-$ ions left in the solution.

This error source is not significant with a single etching batch. If several etching batches are carried out without replacing the KOH solution, the cumulative error will yield unacceptable results.

If this error is to be compensated for by measurements, the $OH^-$ concentration has to be measured either directly or indirectly. The indirect way involves measuring the silicon concentration and subtracting that from the total concentration, which requires two independent measurements.

The economy behind making a reusing or recycling system relies on the high cost of obtaining and disposing of chemicals. This cost has to be balanced with the added cost of the measurement system required in measuring the concentration with sufficient accuracy.

The measurement system should also be care-free and require very little maintenance apart from possible regular calibration. The system should also be physically small enough to be installed in a process station, and it should measure the concentration in-line, i.e. directly from the bath or at the recycling pump.

As the instrument is used in a semiconductor process, no metal parts may touch the process liquid. Plastics, ceramics and glasses are allowed.

The concentration range of KOH in typical etching process is between 0.15 and 0.4 (15% and 40%) w/w. The amount of pure silicon dissolved into the bath is roughly 0.001 w/w (0.1%) per batch. This translates into 0.005 w/w (0.5%) of $K_2H_2SiO_4$.

The problem to be solved can be briefly described so that in the prior art there exists no practical method for measuring the active KOH concentration in a KOH etching process. Main problems in the prior art methods are high costs and inaccuracy.

The object of the invention is to obtain a practical method for a method for in-line measuring the active KOH concentration in a KOH etching process. The object is achieved with the present invention. The invention is characterized in that the total concentration of KOH bath is measured by using a refractometer and the measurement result is corrected by the estimated $K_2H_2SiO_4$ concentration.

The invention offers a simple, reliable and sufficiently accurate measurement method thus solving the problem of the prior art, i.e. creating a useful method in a situation that no practical method exists in the prior art.

BRIEF DESCRIPTION OF THE DRAWINGS

In the following the invention will be described in more detail by means of examples described in the attached drawing, in which.

DESCRIPTION OF THE INVENTION

The background of the invention is described firstly by looking multi-component measurements in general. In order to measure all concentrations in a solution with n components, at least n−1 independent measurement results are needed. With a simple binary solution, e.g. pure KOH in water, one measurement is sufficient. In the case of KOH etching, the solution is a tertiary solution with water, KOH and $K_2H_2SiO_4$. Two independent measurement results are required.

If there are two measurement results, a and b which both depend on the KOH and $K_2H_2SiO_4$ concentrations, the concentrations may be solved by using the measurement results. However, the two different measurements must be different functions of concentrations. In practice, the difference between the two measurements has to be quite significant to give sufficiently accurate results.

Figure 1:
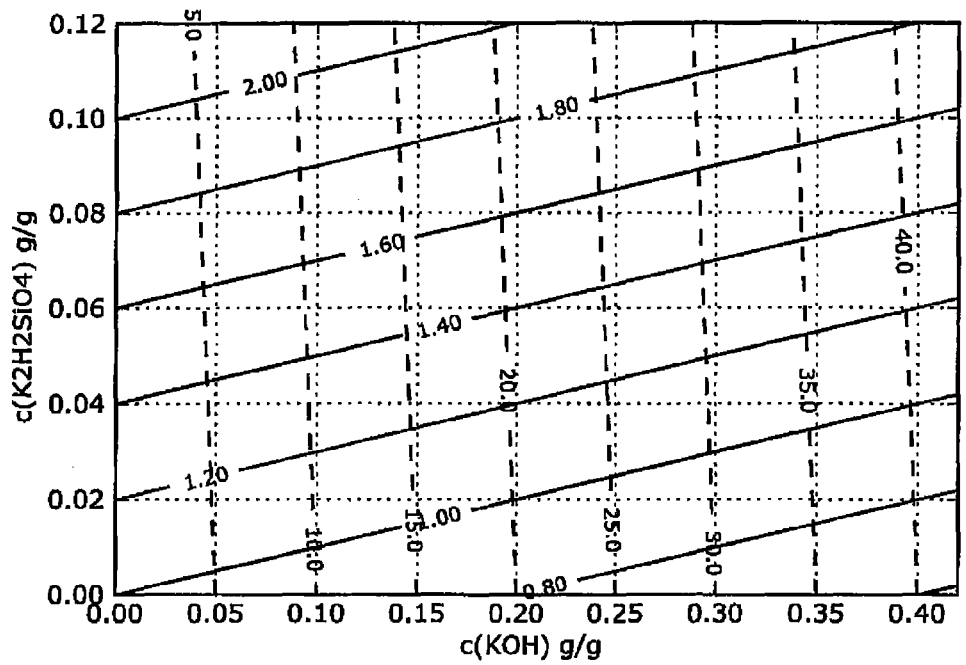
FIG. 1 shows output signals from two different measurement methods in an ideal case.

One way to illustrate this is to use equivalue curves. In FIG. 1 the two axes represent the concentration of KOH and $K_2H_2SiO_4$. The output values of two different (imaginary) measurement methods (a: dash lines, b: solid lines) are drawn in the picture. All points on a single curve represent the same output value from a measurement.

In the case of FIG. 1 a reacts mainly to KOH, and there is only a slight error coming from $K_2H_2SiO_4$ (increasing concentration of $K_2H_2SiO_4$ increases a). Signal b reacts mainly to $K_2H_2SiO_4$, and there is only a small negative error coming from KOH. As the curves are almost perpendicular, a small error in one measurement does not change the result significantly. For example, if a=25.0 and b=1.40, the concentrations can be solved to be c(KOH)=0.24 and c($K_2H_2SiO_4$)=0.065. Small errors in either a or b do not cause large errors in concentration.

Figure 2:
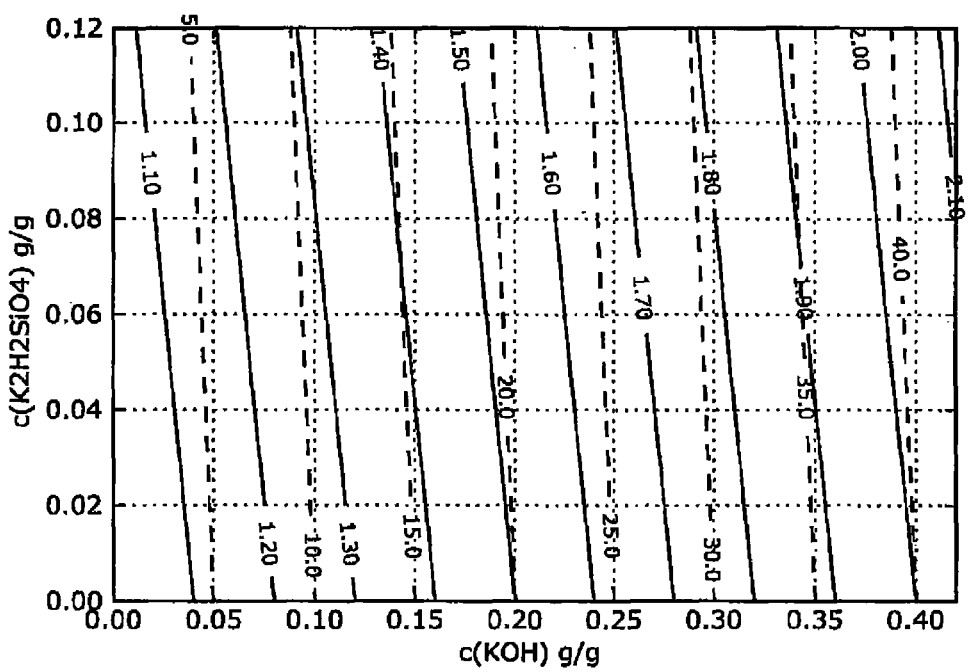
FIG. 2 shows output signals from two different measurement methods in a non-ideal case.

Unfortunately, most measurements tend to react the same way to both chemicals; output value increases with increasing concentration of either chemical. FIG. 2 depicts this situation. Both a and b have an increasing value with increasing concentrations. Measurement b is more sensitive to $K_2H_2SiO_4$ than a, but the sensitivity difference is not very large. It is still mathematically possible to solve the concentrations from a and b, but the real-world accuracy is poor. For example, when a=15.0 and b=1.40, the concentrations are c(KOH)=0.14 and c($K_2H_2SiO_4$)=0.072. A small change in either a or b changes the concentrations so much that the additional measurement has very little value.

In practice, the curves are not linear, but the same ideas apply. If the two sets of equivalue curves are parallel in some point of the graph, the concentrations cannot be solved. The larger the angle between the curves is, the more accurate the results are.

The invention is a result of a project in which thoughts were put to look into the feasibility of active KOH measurement with known process measurement methods and their combinations. The most promising methods have been chosen in the following for closer study.

In the following discussion the measurement methods have been divided into physical and chemical properties. The border between these two types is difficult to draw, but here the division is such that the physical measurement methods do not rely on any chemical or electrochemical reactions in the measurement system itself.

The physical properties of a medium can be divided into optical, thermodynamic and mechanical properties. All of these properties have associated measurement methods, which are briefly discussed below.

Optical properties describe how light behaves in a medium. The definition of light is often restricted to electromagnetic radiation visible to human eye, but in this discussion a broader definition is used; optical measurement methods are methods, which use optical technology. In practice, shorter wave UV (ultra-violet) and longer wave NIR (near-infra-red) and IR (infra-red) instruments are optical instruments by their construction.

Optical measurements are reliable and accurate in general. There are several possibilities in making the measurement insensitive to aging, and the measurement result is directly in electrical form. Optical measurements are also non-invasive, and the only surface in contact with the medium is the optical window. Corrosion problems are rare and in a well-designed instrument they can be overcome with suitable material choices.

In the case of KOH etching the medium is homogeneous, i.e. its optical properties are similar throughout the liquid. There may be hydrogen or air bubbles, but the solution itself is not an emulsion or does not contain a significant amount of particles. This rules out all turbidity (fogginess) measurements.

There are four different optical properties in a homogeneous medium: refractive index, absorptance, optical activity, and fluorescence.

Refractive index describes the optical density of a medium. The refractive index is defined as the speed of light in vacuum divided by the speed of light in the medium. Typical values for aqueous solutions are between 1.33 and 1.52. Refractive index depends on the composition of the medium (concentration of its components) and it has a significant temperature dependence.

The refractive index can be measured with a refractometer. A refractometer can be successfully used in measuring the concentration of KOH in aqueous solutions with sufficiently high accuracy (approximately 0.1% w/w).

Process refractometers are readily available also as industry-specific semiconductor models without any metal in the wetted parts (e.g. K-Patents PR-23-M).

A refractometer can be used to measure most binary solutions (two-component solutions), but in multicomponent solutions it is unable to give the concentration of all components separately. On the other hand, refractometers are insensitive to trace impurities, and thus are well-suited to the total concentration measurement.

In this specific measurement case, refractive index measurement provides a reliable measurement of the total concentration of KOH and $K_2H_2SIO_4$ but it cannot distinguish between the two chemicals, i.e. the refractometer measurement needs to be complemented by another measurement, which reacts to KOH and $K_2H_2SiO_4$ in a different way as discussed earlier.

The counterpart of refractive index is absorptance. Absorptance describes the medium's ability to absorb light. Absorptance is highly dependent on wavelength, and it is sensitive to some trace impurities.

Absorptance can be measured at one wavelength or several wavelengths. in the most extensive form, the absorptance is measured at a large number of wavelengths to produce an almost-continuous spectrum. Spectrometry is a powerful analysis measurement, as many chemicals leave a distinctive fingerprint into the spectrum.

It should be noted that as a spectrometer takes a large number of independent measurements at different wavelengths, it can, at least in theory, determine all concentrations in a multicomponent medium without any complementing measurement.

In practice, spectrometry is not at its strongest when the actual concentration of different components in a solution is important. The response of measurement signal to the concentration is highly non-linear (exponential), and the measurement range and accuracy are limited.

In the case of KOH etching it would suffice to have a silicon-specific measurement with rather moderate accuracy. Unfortunately, the spectral peaks of $K_2H_2SiO_4$ are masked by the very strong spectral peaks of water. So, it seems that spectral measurements cannot be used in measuring the silicon concentration.

It is possible to measure the OH⁻ concentration directly with a spectrometer. For example, ABB manufactures a FTIR (Fourier Transform Infra-Red) spectrometer, which is claimed to be able to measure the OH⁻ concentration. However, as the concentration is rather high, the measurement requires a very short path-length and complicated sampling systems, and still the accuracy is not very good. Also, FTIR analyzers require regular maintenance and carry a high cost of acquisition.

Some media are optically active; they rotate the polarization of incoming light clockwise or counterclockwise. In the case of KOH etching, there are no optically active molecules present and traditional polarimetry cannot be applied.

In some cases even optically inactive liquids rotate the polarization when they are under stress (highly turbulent flow or high flow rates). This tends to be more common in highly viscous liquids. The KOH etchant does not exhibit this property to any significant extent.

Fluorescence refers to the property of a medium to emit lower-energy photons when it is illuminated with higher-energy radiation. In practice, many organic molecules emit yellow light when they are illuminated with blue or ultraviolet light. The KOH etchant does not have this property, at least not enough to use it in a measurement.

Thermodynamically a material has three measurable properties: heat conductivity, heat capacity, and vapor pressure. All of these can be measured, and all of them depend on the concentration of dissolved material.

The heat capacity and conductivity of the KOH etchant do not seem to depend very much on the silicon content. Measuring the heat conductivity and capacity of a liquid is also rather difficult as an in-line measurement. These thermodynamic properties do not offer any practical solution to the concentration measurement problem.

The vapor pressure of a liquid tends to decrease when impurities are dissolved into the liquid. This decrease of vapor pressure can be seen either directly in the partial pressure of saturated vapor over the liquid surface or indirectly as an increase in the boiling point or decrease in the melting point.

There are several possible measurement arrangements to measure the vapor pressure. A single pressure sensor can be used in an evacuated chamber to measure the partial pressure of water directly. The boiling point can be measured, e.g., by heating the liquid with a suitable chosen power, and the freezing point by using a chilled mirror.

Dissolved $K_2H_2SiO_4$ decreases the vapor pressure significantly, and this decrease could be measured. However, as also KOH decreases the vapor pressure, the effect of $K_2H_2SiO_4$ is small in the net depression of vapor pressure. As discussed earlier, this is not a desirable property. In practice, the behavior of vapor pressure measurement and refractive index are so similar that no useful two-component measurement can be realized by their combination.

The KOH solution is visibly more viscous than pure water. The same applies to the solution of KOH and $K_2H_2SiO_4$. This hints to the possibility of using either viscosity or surface tension measurement to distinguish between KOH and $K_2H_2SiO_4$. One possibility lies in the dynamic viscosity (viscosity changing as a function of shear rate).

Surface tension measurement from a continuous process does not give very accurate results. Even with a stationary sample the surface tension measurement does not give any useful results; $K_2H_2SiO_4$ does not have a significantly stronger or weaker effect than KOH on the surface tension.

Viscosity is a highly non-linear phenomenon both as a function of concentration and temperature. The viscosity of pure water at room temperature is approximately 1 mPas. At 20% KOH the viscosity is 1.6 mPas and at 40% the value is approximately 4.0 mPas. So, the viscosity of the etchant is radically different from that of water.

Many viscous liquids are non-Newtonian, i.e. their measured viscosity depends on the shear rate (velocity). Measurements with a high-precision rotary viscometer did not reveal this behavior either with pure KOH or with KOH and $K_2H_2SiO_4$. By these measurements it can be assumed the etchant is a Newtonian liquid, and the dynamic viscosity cannot be used.

Measurements with a capillary viscometer reveal the viscosity behavior of KOH and $K_2H_2SiO_4$ is different in the concentration region of interest. The effect of $K_2H_2SiO_4$ is more linear than that of KOH mainly because of the narrower concentration range.

Figure 3:
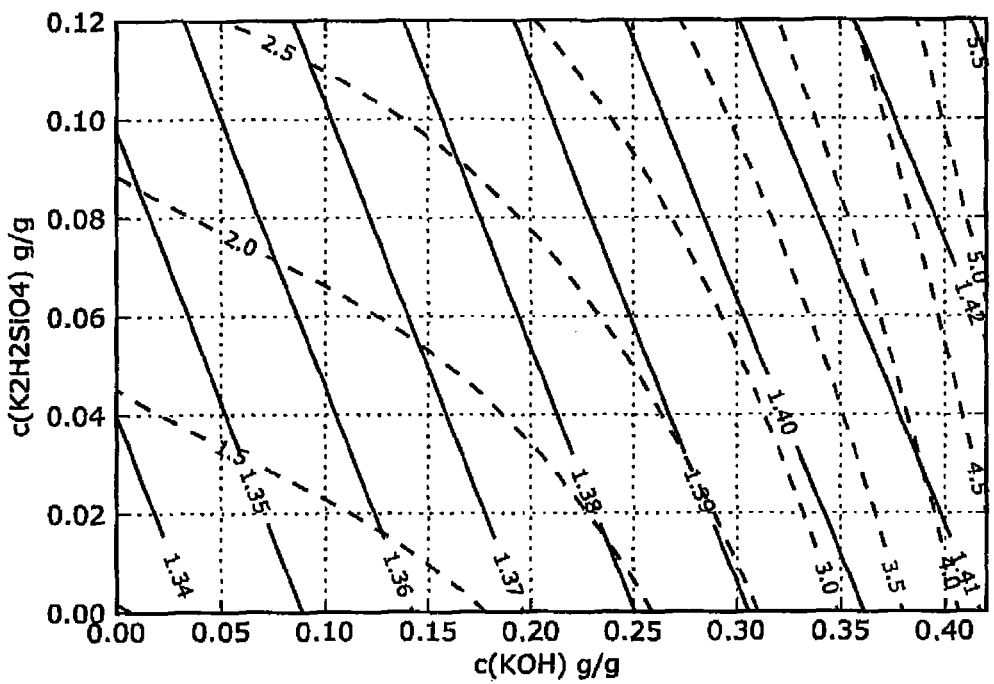
FIG. 3 shows the viscosity and refractive index as functions of KOH and $K_2H_2SiO_4$ concentrations.

FIG. 3 depicts the refractive index (solid line) and viscosity (dashed line) behavior of the etchant. By looking at the angle between the curves, it seems that there are regions where the two measurements can be used to solve the concentrations, especially at low end of c(KOH). Unfortunately, at a very important region of interest (around c(KOH)=0.32 and c($K_2H_2SiO_4$)=0.02) the measurement is impossible as the curves are parallel.

With chemical and electrochemical measurements, there is a direct interaction between the measurement system and the medium under measurement. There are numerous laboratory measurements, which involve a chain of reactions to indicate or measure some property of the liquid. In general, these methods are not directly applicable to automated process measurements. Thus, the discussion below is limited to electrochemical reactions and simple indicator reactions.

There are several electrochemical measurement methods, the simplest being conductivity. Conductivity measurement is not a very useful measurement in the case of highly conductive solutions. Due to the high concentration of KOH the solution has high electric conductance, and the small changes due to KOH being transformed into $K_2H_2SiO_4$ are not significant enough. Also, the measurement is not selective, so that both KOH and $K_2H_2SiO_4$ increase the conductivity.

A pH measurement is in principle a measurement of active $H^+$-ions. As the product of $H^+$ and $OH^-$ ion concentrations is constant in an aqueous solution, the $OH^-$ concentration can be determined from the pH value. However, the pH value of the solution is very high (well above 14), so that the $OH^-$ concentration cannot be determined in practice. Very few pH sensors withstand the environment, and the output signal is logarithmic.

In addition to pH measurement there are some other ion-selective electrochemical measurement methods. No silicon-selective measurements available.

Some chemical properties, e.g. pH, can be indicated by using suitable indicator chemicals. These chemicals can be either free in a solution or bound to some host matrix. Optical indicators are straightforward to measure, and indicator molecules do not need any calibration themselves.

It seems, however, that in this application the good properties of indicators cannot be used. There are no known colour indicators for silicon, using free indicators would require an automatic titration system, and matrix-bound indicators are unlikely to survive in the caustic environment.

When seeing through the matters above it can be said that the theoretical and empirical research carried on the problem of measuring active $OH^-$ in KOH etching bath did not find any practical measurement solution.

Refractometry provides a robust measurement method for pure KOH solutions. The downside is that a refractometer gives only one measurement point, and the effect of KOH and $K_2H_2SiO_4$ cannot be separated. If one concentration is known, the other can be calculated with high accuracy.

Spectrometry is the only method providing direct OH⁻ ion concentration measurement. However, the cost of equipment is high, it requires a lot of maintenance, and the accuracy is not as good as required.

All single-variable measurements (e.g., conductivity, viscosity, etc.) give much the same information as refractometry but with clumsier measurement arrangements and less satisfactory accuracy. None of the methods under research, apart from refractometry, can reach the 0.1% specification in KOH concentration.

All methods seem to react similarly towards KOH and $K_2H_2SiO_4$. This makes using a combination of two different methods impractical.

Despite the difficulties in finding a suitable measurement method as told above, the etch rate can still be determined on-line if one of the concentrations is known. If the $K_2H_2SiO_4$ concentration is known, satisfactory results can be obtained even if the concentration is known with a relatively low accuracy, as the $K_2H_2SiO_4$ concentration is much lower than the KOH concentration. According to the basic idea of the invention a refractometer will give the total concentration of KOH and $K_2H_2SiO_4$, and the measurement result is then corrected by the estimated $K_2H_2SiO_4$ concentration.

The etching process itself is straight-forward. The amount of potassium ($K^+$) does not change in the process. This leaves only two variables; the amount of water, which may change due to evaporation and in the reaction, and the amount of silicon. The amount of silicon can be estimated when the number and type of wafers etched in the solution is known. The only remaining variable (amount of water) can be measured with a refractometer.

It is estimated that one batch of wafers results in 1 g/l of pure silicon dissolved into the bath. When this is translated into $K_2H_2SiO_4$, the number is roughly 6 g/l or 5 g/kg (0.005 w/w). It can be estimated that for ten consecutive batches in the same bath, the concentration rises up to 0.05 w/w.

As the effect of $K_2H_2SiO_4$ on the refractive index is similar to that of KOH, the accuracy required in $K_2H_2SiO_4$ determination is approximately 1:50 of the maximum concentration (an error equivalent to 0.001 w/w of KOH).

The accuracy in determining the $K_2H_2SiO_4$ concentration described above can be reached without any measurements by simple balance calculations. The amount of silicon dissolved from a wafer depends on two factors; the wafer design and the etch depth. The etch depth is highly controlled, and the design parameters (the amount of silicon designed to be removed) can be obtained from the designers.

Figure 4:
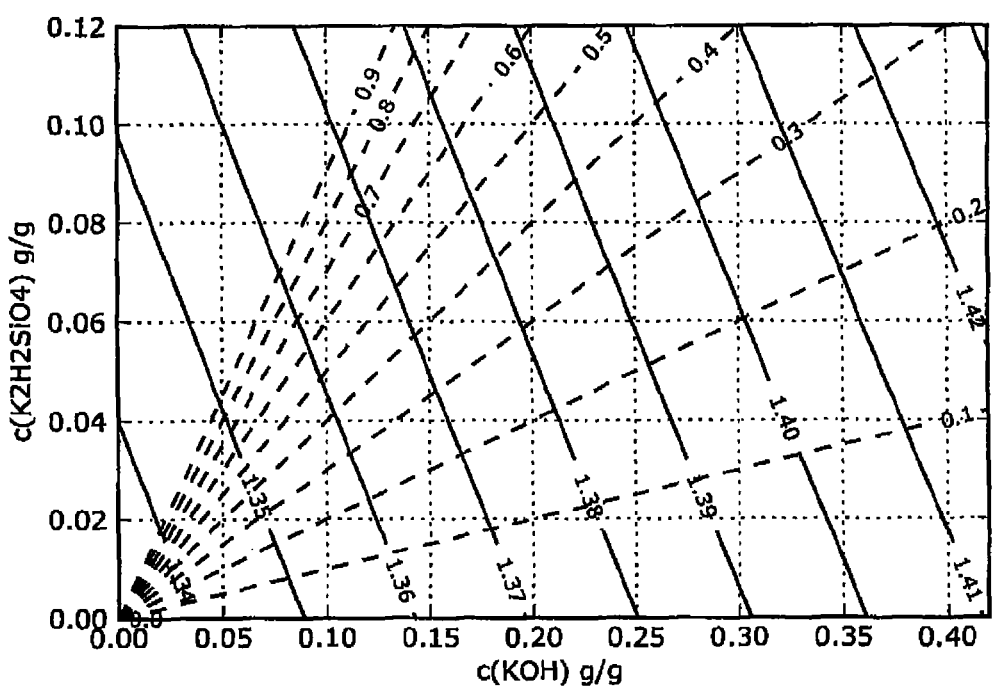
FIG. 4 shows the $K_2H_2SiO_4$/KOH ratio and refractive index as functions of KOH and $K_2H_2SiO_4$ concentrations.

As the total amount of $K^+$ in the bath can be determined from the initial refractive index and volume, the total amount of $K_2H_2SiO_4$ and KOH can be estimated at any time during the process. The amount of water may change, but that does not change the ratio of $K_2H_2SiO_4$ and KOH. FIG. 4 shows the situation graphically. The curves formed by dashed lines depict the different $K_2H_2SiO_4$/KOH ratios and the solid line curves are the equivalue curves for the refractive index. The situation is almost ideal, the two sets of curves are almost perpendicular.

The system is slightly prone to cumulative errors. After a certain number of batches the estimate of dissolved silicon becomes less accurate, which increases the uncertainty in the $K_2H_2SiO_4$/KOH ratio. However, the method should allow several batches to be etched in the same etchant without introducing any extra measurements. A realistic estimate of the number of batches is 10.

The invention claimed is:

1. A method for in-line measurement of an active KOH concentration in a KOH etching process in which silicon hydroxide is produced by a reduction reaction according to the formula:

$$2K^+ \text{(aq.)} + 2OH^- \text{(aq.)} + 2H_2O + Si \rightarrow 2K^+ \text{(aq.)} + H_2SiO_4^{2-} \text{(aq.)} + 2H_2 \text{(g)},$$

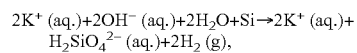

the method comprising:
measuring a total concentration of KOH and $K_2H_2SiO_4$ in an etch bath using a refractometer,
estimating a concentration of $K_2H_2SiO_4$ in the etch bath, and
determining the active KOH concentration in the etch bath using the measured total concentration of KOH and $K_2H_2SiO_4$ and the estimated $K_2H_2SiO_4$ concentration,
wherein the concentration of $K_2H_2SiO_4$ is estimated after processing about ten or less batches of silicon and estimating the concentration of $K_2H_2SiO_4$ comprises performing a balance calculation using an estimated amount of Si dissolved into the bath from each batch.

2. A method for in-line measurement of an active KOH concentration in a KOH etching process in which silicon hydroxide is produced by a reduction reaction according to the formula:

$$2K^+ \text{(aq.)} + 2OH^- \text{(aq.)} + 2H_2O + Si \rightarrow 2K^+ \text{(aq.)} + H_2SiO_4^{2-} \text{(aq.)} + 2H_2 \text{(g)},$$

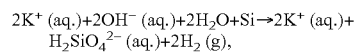

the method comprising:
measuring a total concentration of KOH and $K_2H_2SiO_4$ in an etch bath using a refractometer,
estimating a concentration of $K_2H_2SiO_4$ in the etch bath, and
determining the active KOH concentration in the etch bath using the measured total concentration of KOH and $K_2H_2SiO_4$ and the estimated $K_2H_2SiO_4$ concentration,
wherein the concentration of $K_2H_2SiO_4$ is estimated after etching a number of wafers having a known design to a controlled etch depth and estimating the concentration of the of $K_2H_2SiO_4$ comprises calculating the estimated amount of $K_2H_2SiO_4$ in solution from the number of the etched wafers, the design of the etched wafers, and the etch depth of the etched wafers.

* * * * *